US010349865B2

(12) United States Patent
Roland (10) Patent No.: US 10,349,865 B2
(45) Date of Patent: Jul. 16, 2019

(54) METHOD, LOCAL COIL AND MAGNETIC RESONANCE APPARATUS FOR MAGNETIC RESONANCE IMAGING

(71) Applicant: Siemens Aktiengesellschaft, Munich (DE)

(72) Inventor: Joerg Roland, Hemhofen (DE)

(73) Assignee: Siemens Aktiengesellschaft, Munich (DE)

( * ) Notice: Subject to any disclaimer, the term of this patent is extended or adjusted under 35 U.S.C. 154(b) by 1028 days.

(21) Appl. No.: 14/805,666

(22) Filed: Jul. 22, 2015

(65) Prior Publication Data

US 2016/0025830 A1    Jan. 28, 2016

(30) Foreign Application Priority Data

Jul. 22, 2014   (DE) .................. 10 2014 214 266

(51) Int. Cl.
| | | |
|---|---|---|
| G01R 33/48 | (2006.01) | |
| A61B 5/055 | (2006.01) | |
| A61B 5/00 | (2006.01) | |
| G01R 33/28 | (2006.01) | |
| G01R 33/54 | (2006.01) | |
| G01R 33/565 | (2006.01) | |
| A61B 90/00 | (2016.01) | |
| G01R 33/3875 | (2006.01) | |

(52) U.S. Cl.
CPC ............ *A61B 5/055* (2013.01); *A61B 5/4312* (2013.01); *A61B 90/39* (2016.02); *G01R 33/28* (2013.01); *G01R 33/543* (2013.01); *G01R 33/56563* (2013.01); *A61B 2090/3958* (2016.02); *G01R 33/3875* (2013.01)

(58) Field of Classification Search
USPC .......................... 324/300–322; 600/407–435; 382/128–131
See application file for complete search history.

(56) References Cited

U.S. PATENT DOCUMENTS

| | | | | |
|---|---|---|---|---|
| 6,552,541 B2 * | 4/2003 | Nauerth | ............. | G01R 33/4625 |
| | | | | 324/307 |
| 2003/0006770 A1 * | 1/2003 | Smith | ..................... | F23C 6/045 |
| | | | | 324/309 |
| 2005/0080333 A1 | 4/2005 | Piron et al. | | |
| 2007/0167758 A1 * | 7/2007 | Costello | ................. | A61B 5/055 |
| | | | | 600/437 |
| 2007/0233195 A1 * | 10/2007 | Wahlstrand | .......... | A61N 1/0529 |
| | | | | 607/2 |
| 2010/0099978 A1 | 4/2010 | Geppert et al. | | |

(Continued)

*Primary Examiner* — Tung X Nguyen
*Assistant Examiner* — Robert P Alejnikov, Jr.
(74) *Attorney, Agent, or Firm* — Schiff Hardin LLP (57) ABSTRACT

In a method, a local coil, and an apparatus for magnetic resonance imaging, an examination subject is situated in a patient receiving area of the apparatus, together with at least one marker element. The apparatus is operated to perform a radio-frequency excitation of the at least one marker element, and to read out magnetic resonance signals that are emitted by the at least one marker element. An image data acquisition scanner of the magnetic resonance apparatus is adjusted using the magnetic resonance signals that have been read out. Magnetic resonance image data are acquired from the subject by operation of the adjusted image data acquisition scanner.

11 Claims, 2 Drawing Sheets

(56) References Cited

U.S. PATENT DOCUMENTS

| | | | |
|---|---|---|---|
| 2011/0046475 A1 | 2/2011 | Assif et al. | |
| 2013/0249552 A1* | 9/2013 | Imamura | G01R 33/583 |
| | | | 324/309 |
| 2013/0278263 A1* | 10/2013 | Huang | G01R 33/5611 |
| | | | 324/309 |

* cited by examiner

METHOD, LOCAL COIL AND MAGNETIC RESONANCE APPARATUS FOR MAGNETIC RESONANCE IMAGING

BACKGROUND OF THE INVENTION

Field of the Invention

The invention concerns a method for magnetic resonance imaging, a local coil for a magnetic resonance apparatus, and a magnetic resonance apparatus.

Description of the Prior Art

In a magnetic resonance apparatus, also referred to as a magnetic resonance tomography system, a subject to be examined, in particular the body of a patient, is normally subjected to a relatively high basic magnetic field, for example 1.5 or 3 or 7 Tesla, by the operation of a basic field magnet. In addition, gradient pulses are activated by a gradient coil unit. Radio-frequency (RF) pulses are then emitted by a suitable antenna arrangement, such as a radio-frequency antenna unit. The RF pulses serve as excitation pulses, which means that the nuclear spins of particular atoms resonantly excited by the radio-frequency pulses are tilted by a defined flip angle with respect to the magnetic field lines of the basic magnetic field. As the nuclear spins relax radio-frequency signals, so-called magnetic resonance signals, are emitted that are received by suitable radio-frequency antennas, and then processed further. Finally, the desired image data can be reconstructed from the raw data thus acquired in this manner.

For a particular measurement, a specific magnetic resonance sequence, also referred to as pulse sequence, is to be transmitted, which is composed of a series of radio-frequency pulses, in particular excitation pulses and refocusing pulses, as well as gradient pulses appropriately coordinated therewith, activated in different gradient axes along different spatial directions. Readout windows chronologically appropriate for this purpose are set, which predetermine the periods of time in which the induced magnetic resonance signals are acquired.

With such a pulse sequence, a measurement (data acquisition) by the magnetic resonance apparatus is typically carried out by the scanner of the magnetic resonance apparatus. Prior to the measurement, an adjustment of the scanner takes place, which can include, for example, setting the resonance frequency for the scanner and/or adjust shimming components by using shim settings.

SUMMARY OF THE INVENTION

An object of the invention is to enable improved adjustment of a scanner of a magnetic resonance apparatus for a measurement with the magnetic resonance apparatus.

The invention encompasses a method for magnetic resonance imaging of a subject under examination by operation of a magnetic resonance apparatus that has a scanner with a patient receiving area in which are arranged the subject under examination and at least one marker element. The method includes the steps of operating the scanner to perform a radio-frequency excitation of the at least one marker element, also operating the scanner to read out magnetic resonance signals that are emitted by the at least one marker element after excitation thereof, adjusting the scanner of the magnetic resonance apparatus using the magnetic resonance signals that have been read out from the marker, and operating the adjusted scanner to acquire magnetic resonance image data from the subject under examination.

The subject under examination can be a patient, a training person or a phantom. On the basis of the magnetic resonance image data, magnetic resonance images are reconstructed by a computer of the magnetic resonance apparatus. The magnetic resonance images can be presented as an output on a display unit of the magnetic resonance apparatus and/or stored in a database. The patient receiving area is a hollow, cylindrical-shaped opening of the magnetic resonance device. The subject under examination and the at least one marker element are simultaneously positioned in the hollow cylindrical shaped opening.

The at least one marker element is designed in order to emit radio-frequency signals, in other words magnetic resonance signals, after the radio-frequency excitation. The at least one marker element is preferably formed from a material whose atomic nuclei are excited by the radio-frequency excitation and subsequently emit magnetic resonance signals. The at least one marker element advantageously has a defined composition. The defined composition can be stored in a database of the magnetic resonance device. Furthermore, the at least one marker element is secured at a defined position in the patient receiving area. This defined position can be stored in a database of the magnetic resonance device.

The execution of the radio-frequency excitation of the at least one marker element can be performed selectively for the defined position of the at least one marker element. Alternatively or in addition, the radio-frequency excitation can exhibit an excitation frequency which is matched to a resonance frequency of the at least one marker element. A localized radio-frequency excitation of the at least one marker element can thus take place. It is thereby possible to ensure that only the magnetic resonance signals are read out which are emitted by the at least one marker element. It is also conceivable that magnetic resonance signals are read out from a larger excitation region. The magnetic resonance signals that are emitted by the at least one marker element are then advantageously segmented subsequently, in particular using the known defined position of the at least one marker element.

The magnetic resonance signals that are read out, which are emitted by the at least one marker element, can then be used as input data for adjusting the image data acquisition scanner of the magnetic resonance device. This adjustment can be, for example, setting the resonance frequency for the image data acquisition unit and/or adjusting a shimming component by using shim settings. The adjustment of the image data acquisition scanner can also include further operations as appear expedient to those skilled in the art. After adjustment of the image data acquisition unit, the image data acquisition unit is adjusted for the acquisition of the magnetic resonance image data. The acquisition of the magnetic resonance image data by operation of the adjusted image data acquisition scanner takes place after completion of the adjustment of the image data acquisition scanner.

The inventive method offers the advantage that the adjustment of the image data acquisition scanner can be performed using additional input data, namely the magnetic resonance signals read out. In accordance with the invention, this situation the magnetic resonance signals that are read out are independent of the subject under examination positioned in the patient receiving area because the magnetic resonance signals read out originate from the at least one marker element. In contrast to the subject under examination, the at least one marker element advantageously has a composition and/or position that is/are known a priori. The inventive approach is thus particularly advantageous in the case of examining tissue that has a very different proportional composition from a remainder of the subject under examination, such as, for example, in a breast region of the subject under examination. The at least one marker element thus offers particularly advantageous information that can be used for an adjustment of the image data acquisition unit. The adjustment of the image data acquisition unit thus can be improved through the use of the at least one marker element. The image quality of the magnetic resonance image data acquired by the adjusted image data acquisition scanner can also be improved in such a manner. Optimum settings can then be ascertained directly from the position of the at least one marker element during the adjustment of the image data acquisition scanner. The settings can be extrapolated from the position of the at least one marker element to other spatial regions and/or be used as a starting point for the adjustment of the image data acquisition unit for other spatial regions.

In an embodiment, the acquisition of the magnetic resonance image data takes place from a breast region of the subject under examination. In conventional approaches, the breast region of the subject under examination typically presents problems for an adjustment of the image data acquisition scanner. The reason for this is the differing proportional composition of the breast depending on the subject under examination, for example composed of fatty tissue, aqueous tissue, silicone, etc. The creation of shim settings for the breast region of the subject under examination is also typically problematical in conventional approaches because the breast region is positioned in the coronal direction perpendicular to a support surface of the subject under examination, typically outside the isocenter of the basic magnetic field of the magnetic resonance apparatus. Furthermore, shim settings must be determined for two separate regions for the breast region of the subject under examination. By using the at least one marker element the image data acquisition scanner can be adjusted particularly advantageously for the acquisition of magnetic resonance image data from the breast region of the subject under examination. For this purpose, the at least one marker element is advantageously located spatially in the immediate vicinity of the breast region of the subject under examination. This can mean that the at least one marker element is located, for example, at a distance of at most 20 cm, advantageously at most 10 cm, particularly advantageously at most 5 cm, from a surface of a breast of the subject under examination. If the acquisition of the magnetic resonance image data from the breast region of the subject under examination takes place with the use of a breast coil, the at least one marker element is advantageously integrated into the breast coil. In contrast to tissue in the breast region of the subject under examination, the at least one marker element has a defined composition. The adjustment of the image data acquisition unit on the basis of the magnetic resonance signals emitted by the marker element thereby enables a reliable adjustment of the image data acquisition unit. This can be better than an adjustment of the image data acquisition unit using only magnetic resonance signals emitted from the breast region of the subject under examination for the adjustment of the image data acquisition unit.

In another embodiment, the at least one marker element includes a defined proportion of at least one substance, wherein information concerning a level of the defined proportion of the at least one substance is stored in a database and the adjustment of the image data acquisition unit involves use of the information concerning the level of the defined proportion of the at least one substance. The at least one substance can, for example, be or include water, fat, air, bone material, etc. On the basis of information concerning the level of the defined proportion of the at least one substance it is for example possible to calculate the resonance frequency of the at least one marker element. The resonance frequency can be, as described below, employed for a frequency adjustment of the image data acquisition scanner. As a result of the defined composition of the at least one marker element, the at least one marker element is particularly advantageously suited for the adjustment of the image data acquisition unit. In contrast to a body tissue of the subject under examination, the composition of the marker element is known, which means that the magnetic resonance signals emitted by the marker element can be evaluated using its known composition. For this purpose, the information concerning the level of the defined proportion of the at least one substance can be loaded from the database for the adjustment of the image data acquisition unit.

In another embodiment, the at least one substance is composed of water and/or fat. The at least one marker element can, for example, consist entirely of water or fat. Alternatively, a proportional design of the at least one marker element composed of water and fat is also conceivable. The percentage proportions of water and fat can be matched to the respective application. It is also advantageous for multiple marker elements to be employed. The multiple marker elements can then have differing proportional compositions of water and/or fat. The at least one marker element can naturally also include further substances other than water and fat. The use of water and/or fat as the substance(s) of the at least one marker element does, however, advantageously enable the at least one marker element to be matched to tissue of the body of the subject under examination.

In a further embodiment, the adjustment of the image data acquisition scanner involves a frequency adjustment of the image data acquisition scanner that is carried out using the magnetic resonance signals that have been read out. In this embodiment, the frequency adjustment of the image data acquisition scanner is typically done prior to the acquisition of the magnetic resonance image data by operation of the adjusted image data acquisition scanner. The frequency adjustment typically involves setting a frequency of a radio-frequency antenna unit of the image data acquisition scanner. The excitation frequency of the radio-frequency antenna unit is set in such a manner so that it matches the Larmor frequency of protons in the field of examination. The frequency adjustment is typically dependent on a distribution of aqueous tissue and/or fatty tissue in the subject under examination because the Larmor frequency of the protons in aqueous tissue differs from the Larmor frequency of the protons in fatty tissue. The frequency adjustment in this case can involve an adjustment of the frequency of the image data acquisition scanner to a baseline of the water frequency. As described above, the at least one marker element has a defined composition for use in the frequency adjustment. The use of the magnetic resonance signals that are emitted by the at least one marker element in this manner enables an exact setting of the frequency of the image data acquisition scanner. The frequency of the image data acquisition scanner can in this manner be matched to the resonance frequency of protons in water and/or fat.

In another embodiment, the readout of the magnetic resonance signals involves a readout of a measuring frequency at a position of the at least one marker element, with a comparison being made of the measuring frequency, and a known marker element frequency of the at least one marker element. The frequency adjustment is the completed using a result of this comparison. In this situation the marker element frequency is known, such as by being determined from the defined proportion of water and/or fat in the marker element. The marker element frequency can alternatively or additionally be stored in a database. Knowledge of the marker element frequency constitutes an advantage in using the at least one marker element compared with using body tissue of the subject under examination in the frequency adjustment. This is because the body tissue of the subject under examination typically has an unknown composition, meaning that the body tissue frequency typically cannot be determined exactly. The fact that the frequency adjustment takes place using the result of the comparison means that an excitation frequency of the radio-frequency antenna unit is adapted during the frequency adjustment such that the measuring frequency that is read out from the at least one marker element is adapted to the marker element frequency. A particularly precise frequency adjustment can thereby be carried out and the image quality of the magnetic resonance image data acquired by operation of the adjusted image data acquisition unit can be improved.

In another embodiment, the adjustment of the image data acquisition scanner takes place using shim settings, with the shim settings being generated using the magnetic resonance signals that have been read out. Shim settings can be settings for controlling a shim component of the magnetic resonance device. For example, the shim settings can specify a power distribution, possibly time-dependent, of the currents in shim coils of a shim unit. Calculation of the shim settings thus can involve a calculation of shim currents. The shim settings are calculated prior to acquisition of the magnetic resonance image data. The shim settings can be used to compensate for inhomogeneities in the basic magnetic field of the magnetic resonance apparatus, such as inhomogeneities caused by the subject under examination. The at least one marker element can in this case provide defined information for generating the shim settings. The magnetic resonance signals read out, which are emitted by the at least one marker element, can, in addition to a tissue distribution in the subject under examination, thus constitute an advantageous information source for generating the shim settings.

In a further embodiment, the generation of the shim settings includes ascertaining a local homogeneity of the basic magnetic field of the magnetic resonance apparatus (scanner) at a position of the at least one marker element on the basis of the magnetic resonance signals read out, and calculating the shim settings on the basis of the ascertained local homogeneity of the basic magnetic field. The shim settings that are generated can be used during acquisition of the magnetic resonance image data in order to control the shim unit. It is particularly advantageous in this case that the local homogeneity of the primary magnetic field is measured at the defined position of the at least one marker element, because the at least one marker element represents reproducible measurement conditions for determining the local homogeneity of the basic magnetic field.

In another embodiment, basic shim settings are calculated on the basis of the ascertained local homogeneity of the primary magnetic field, and the calculation of the shim settings further involves a fine adjustment of the basic shim settings. The calculation of the basic shim settings can initially be based on a calculation of local shim settings for the position of the at least one marker element. The local homogeneity values ascertained at the position of the at least one marker element can also be interpolated to the remainder of the field of examination for the calculation of the basic shim settings. The basic shim settings represent an advantageous starting point for the calculation of the shim settings. The basic shim settings can represent, for example, an advantageous start value for the calculation of the shim settings. The shim settings can then be calculated in a particularly efficient manner in terms of saving computing time.

In a further embodiment, the calculation of the shim settings is performed dependent on at least one boundary condition. The at least one boundary condition can require that a local minimum homogeneity of the basic magnetic field to exist at the position of the at least one marker element. The minimum homogeneity can be defined as a maximum deviation from a local homogeneity and/or as a maximum tolerable inhomogeneity of the basic magnetic field. In contrast to the approach described above, in this case the shim settings are advantageously calculated in one pass. The shim settings are then calculated such that a minimum homogeneity of the basic magnetic field is present at the position of the at least one marker element during the acquisition of the magnetic resonance image data. The minimum homogeneity may depend on the particular application. The minimum homogeneity can also be predetermined by a user, or automatically. The at least one marker element represents a particularly advantageous location for checking the homogeneity of the primary magnetic field because the at least one marker element ensures defined and reproducible measurement conditions.

The invention furthermore encompasses a local coil for a magnetic resonance apparatus, the local coil including at least one marker element that has a defined proportion of at least one substance. In this context, a "local coil" should be understood as being a local magnetic resonance radio-frequency antenna unit, which is arranged directly around a body area to be examined, or at a minimal distance therefrom, of the subject under examination. The local coil is designed in order to receive magnetic resonance signals. In special applications the local coil can also be designed in order to emit radio-frequency pulses. The position of the local coil within the patient receiving area is in this case dependent on the body area to be examined and/or on anatomy of the subject under examination. The at least one marker element can be embodied as a liquid-filled container, for example as a capsule and/or sphere. The at least one marker element can also be composed completely of a magnetic resonance signal generating solid. Such a local coil thus is advantageously employed in the method according to the invention for magnetic resonance imaging.

In an embodiment of the local coil, the local coil has a coil holder on which the at least one marker element is secured. The coil holder can be designed as a retaining fixture for coil elements of the local coil. Securing the at least one marker element to the coil holder enables a particularly advantageous positioning of the at least one marker element because the at least one marker element can be secured particularly close to a field of examination for acquisition of the magnetic resonance image data. The at least one marker element can also be integrated into the coil holder, whereby a particularly positive and space-saving positioning of the at least one marker element is enabled.

In another embodiment of the local coil, the local coil is designed as a breast coil, which has a first breast receiving area and a second breast receiving area. The breast coil is in particular a radio-frequency local coil. The breast coil is so as to receive radio-frequency signals. The breast coil can also be designed in special cases so as to emit radio-frequency pulses. For acquisition of the magnetic resonance image data from the breast region of the subject under examination, the subject under examination is typically positioned in the prone position on a patient supporting device of the magnetic resonance apparatus. The breast coil is then likewise advantageously positioned on the patient supporting device. This permits the breasts of the subject under examination to be positioned in the two breast receiving areas of the breast coil. The breast coil has coil elements that advantageously are immediately adjacent to the two breast receiving areas. Integration of the at least one marker element into the breast coil permits a particularly advantageous positioning of the at least one marker element. The local coil can basically also be embodied as a knee coil, head coil, body coil, etc.

In another embodiment of the local coil, the local coil has at least two marker elements, wherein at least one first marker element of the at least two marker elements is arranged on the first breast receiving area and at least one second marker element of the at least two marker elements is arranged on the second breast receiving area. The first and second breast receiving areas each have a depression designed to allow a breast of the subject under examination can be positioned in the depression. In such a manner, each breast is assigned at least one marker element. The at least one marker element can then be used, for example, for generating shim settings for the associated breast region. For each breast of the area under examination, it is thus possible to carry out a customized adjustment of the image data acquisition unit on the basis of the marker element assigned to the respective breast.

In a further embodiment of the local coil the local coil has an axis of symmetry, and the first breast receiving area is arranged on a first side of the axis of symmetry and the second breast receiving area is arranged on a second side of the axis of symmetry, symmetrically to each other with respect to the axis of symmetry. The at least one first marker element and the at least one second marker element also are arranged symmetrically to each other with respect to the axis of symmetry. Magnetic resonance signals that are emitted by marker elements positioned at advantageous locations thus can be used for the adjustment of the image data acquisition unit.

The invention furthermore encompasses a magnetic resonance apparatus having an image data acquisition scanner, an adjustment unit, a control computer, a patient receiving area, and a marker unit having at least one marker element, which is arranged in the patient receiving area. The magnetic resonance apparatus is designed in order to implement the method according to the invention.

The magnetic resonance device is thus designed in order to implement a method for magnetic resonance imaging of a subject under examination which is arranged in the patient receiving area. The image data acquisition scanner is in this case operated by the control computer in order to perform a radio-frequency excitation of the at least one marker element and to read out magnetic resonance signals that are emitted by the at least one marker element as a result of the excitation. The adjustment unit (processor) is designed to adjust the image data acquisition scanner of the magnetic resonance device using the magnetic resonance signals which have been read out. The adjusted image data acquisition scanner is then operated by the control computer to acquire magnetic resonance image data for the subject under examination.

The magnetic resonance apparatus can have further control components that are required and/or advantageous for executing the method according to the invention. Computer programs and further software can be stored in a storage unit of the computer unit and/or of the control computer, by which a processor of the control computer automatically controls and/or executes a process sequence of the method according to the invention.

The advantages of the magnetic resonance apparatus according to the invention and of the local coil according to the invention essentially correspond to the advantages of the method according to the invention, which have been explained above in detail. Features, advantages or alternative embodiments mentioned here are likewise applicable to all aspects of the invention. The functional features of the method are embodied by corresponding object modules, in particular by hardware modules.

DESCRIPTION OF THE PREFERRED EMBODIMENTS

Figure 1:
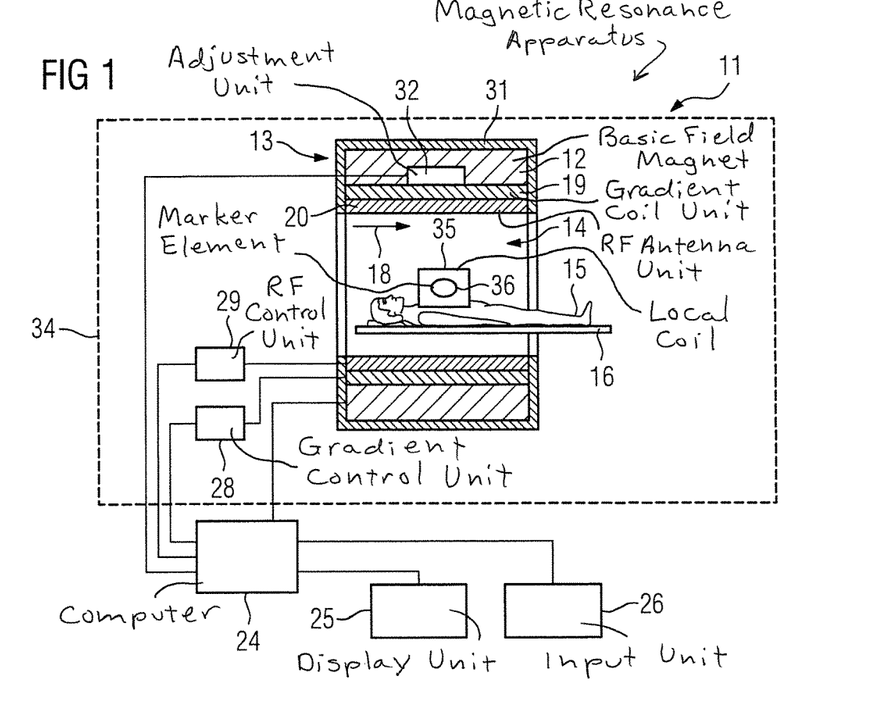
FIG. 1 schematically illustrates a magnetic resonance apparatus according to the invention.

FIG. 1 schematically illustrates a magnetic resonance apparatus 11 according to the invention. The magnetic resonance apparatus 11 has a scanner 13, having a basic field magnet 12 for generating a strong and constant basic magnetic field 18. The magnetic resonance apparatus 11 also has a cylindrical patient receiving area 14 for accommodating a subject under examination 15, a patient 15 in this case. The patient receiving area 14 is enclosed circumferentially in a cylindrical fashion by the magnet unit 13. The patient 15 can be moved into the patient receiving area 14 by a patient supporting device 16 of the magnetic resonance apparatus 11. The patient supporting device 16 has a patient table that is mounted to as to be movable inside the scanner of the magnetic resonance apparatus 11. The magnet unit 13 is shielded externally by housing paneling 31.

The magnet unit 13 furthermore has a gradient coil unit 19 in order to generate magnetic field gradients that are used for spatial encoding during an imaging process. The gradient coil unit 19 is driven by a gradient control unit 28. In addition the scanner 13 has a radio-frequency (RF) antenna unit 20 that in the shown embodiment is designed as a body coil permanently integrated into the scanner 13 of the magnetic resonance apparatus 10. A radio-frequency antenna control unit 29 operates the antenna unit 20 in order to excite nuclear spins to depart from the polarization that arises in the basic magnetic field 18 generated by the basic field magnet 12. The radio-frequency antenna unit 20 is driven by the radio-frequency antenna control unit 29 and radiates radio-frequency magnetic resonance sequences into an examination volume that is essentially formed by the patient receiving area 14. The radio-frequency antenna unit 20 is furthermore embodied in order to receive magnetic resonance signals, in particular emanating from the patient 15.

The magnetic resonance apparatus 11 has a computer 24 for controlling the basic field magnet 12, the gradient control unit 28 and the radio-frequency antenna control unit 29. The computer 24 provides central control of the magnetic resonance apparatus 11, for example, the execution of a predetermined imaging gradient echo sequence. Control information such as, for example, imaging parameters as well as reconstructed magnetic resonance images can be displayed on a display unit 25, for example on at least one monitor, of the magnetic resonance apparatus 11, for a user. In addition the magnetic resonance apparatus 11 has an input unit 26 via which information and/or parameters can be entered by a user during a measurement operation. The computer 24 can include the gradient control unit 28 and/or radio-frequency antenna control unit 29 and/or the display unit 25 and/or the input unit 26.

A marker unit having least one marker element 36 is arranged in the patient receiving area 14. In the case shown the marker element 36 is part of a local coil 35 which in the present case is designed as a breast coil, as an example. In this situation the breast coil is arranged in a breast region of the subject under examination 15. The marker element can naturally also be arranged at a different location in the patient receiving area 14.

The magnetic resonance apparatus 11 furthermore has an adjustment unit 32 that is designed in order to set the image data acquisition scanner 34. The adjustment unit 32 can be designed, for example, in order to perform frequency adjustment of the image data acquisition scanner 13. The adjustment unit 32 can also be set using shim settings for recording magnetic resonance image data by means of the image data acquisition scanner 13. In this situation the adjustment unit 32 is connected to the computer 24 for data exchange. The adjustment unit 32 can also be a part of the computer 24. The magnetic resonance apparatus 11 together with the computer 24, the adjustment unit 32, the image data acquisition scanner 13, the patient receiving area 14 and the marker unit having the at least one marker element 36 is thus designed in order to carry out the method according to the invention.

The magnetic resonance apparatus 11 illustrated can naturally include further components that magnetic resonance apparatuses normally have. The general operation of a magnetic resonance apparatus 11 is known to those skilled in the art, so that a detailed description of the further components is not necessary herein.

Figure 2:
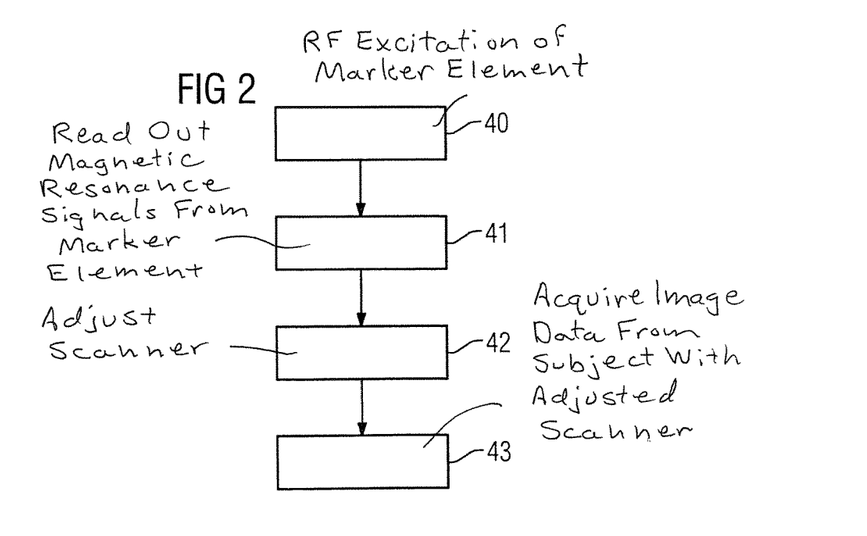
FIG. 2 is a flowchart of a first embodiment of the method according to the invention.

FIG. 2 shows a flowchart of a first embodiment of a method according to the invention for magnetic resonance imaging of a subject under examination 15 by the magnetic resonance apparatus 11, which includes a patient receiving area 14 in which are arranged the subject under examination 15 and at least one marker element 36.

In a first method step 40, an image data acquisition scanner 13, a radio-frequency antenna unit 20 of the image data acquisition scanner 13, performs a radio-frequency excitation of the at least one marker element 36. In a further method step 41, the image data acquisition scanner 13 reads out magnetic resonance signals which are emitted by the at least one marker element 36. In a further method step 42, an adjustment unit 32 adjusts the image data acquisition scanner 13 of the magnetic resonance apparatus 11 using the magnetic resonance signals read out in the further method step 41. In a further method step 43, acquisition of magnetic resonance image data for the subject under examination 15 takes place by means of the adjusted image data acquisition scanner 13.

Figure 3:
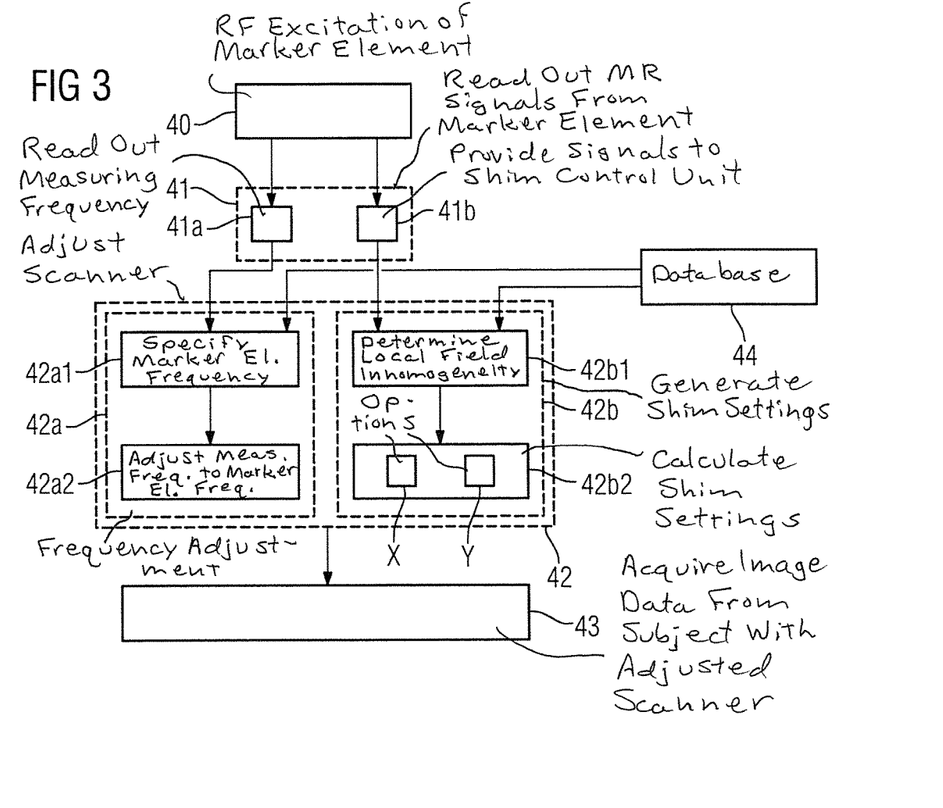
FIG. 3 is a flowchart of a second embodiment of the method according to the invention.

FIG. 3 shows a flowchart of a second embodiment of the method according to the invention.

The following description is restricted essentially to the differences from the exemplary embodiment in FIG. 2, wherein reference is made to the description of the exemplary embodiment in FIG. 2 with respect to method steps remaining the same. Method steps essentially remaining the same are basically numbered using the same reference characters.

The second embodiment shown in FIG. 3 of the method according to the invention includes the method steps 40, 41, 42, 43 of the first embodiment of the method according to the invention according to FIG. 2. In addition, the second embodiment of the method according to the invention shown in FIG. 3 has additional method steps and substeps. Also conceivable is an alternative process sequence to FIG. 3, which has only a part of the additional method steps and/or substeps illustrated in FIG. 2. An alternative process sequence to FIG. 3 can naturally also have additional method steps and/or substeps.

The further method step 41, reading out the magnetic resonance signals, includes a first substep 41a during which a measuring frequency at a position of the at least one marker element 36 is read out by operation of the image data acquisition scanner 13.

The further method step 42, the adjustment of the image data acquisition scanner 13, includes a substep 42a for this purpose, during which a frequency adjustment of the image data acquisition scanner 13 takes place. The frequency adjustment is performed by the adjustment unit 32, in particular a frequency adjustment unit (not illustrated) of the adjustment unit 32. The frequency adjustment is performed using the magnetic resonance signals which have been read out. For this, a marker element frequency can be specified in a substep 42a1 for the at least one marker element 36. In this case the marker element frequency is the resonance frequency of the at least one marker element 36. In the present exemplary embodiment, the at least one marker element 36 includes a defined proportion of at least one substance. Information concerning a level of the defined proportion of the at least one substance is stored in a database 44. In the present case the marker element 36 includes, for example, a defined proportion of water and fat. The information concerning the level of the defined proportion of the at least one substance is used by the frequency adjustment unit for specifying the marker element frequency. In a substep 42a2, the measuring frequency is adjusted to the marker element frequency for the frequency adjustment of the image data acquisition scanner 13. This is done by a result of a comparison of the marker element frequency and the measuring frequency.

The further method step 41 includes a second substep 41b in which the magnetic resonance signals read out are passed to a shim control unit (not illustrated) of the computer 24 of the magnetic resonance apparatus 11.

To this end, the further method step 42, the adjustment of the image data acquisition scanner 13, includes a substep 42b during which a shim unit (not illustrated) of the adjustment unit 32 is set using shim settings for the acquisition of the magnetic resonance image data. In this situation the shim settings are calculated using the magnetic resonance signals which have been read out by the shim control unit. In a substep 42b1, the creation of the shim settings includes ascertaining a local homogeneity of the basic magnetic field 18 of the magnetic resonance apparatus 11 at a position of the at least one marker element 36 on the basis of the magnetic resonance signals that are read out from the maker element 36. In a substep 42b2, the shim settings are calculated on the basis of the ascertained local homogeneity of the basic magnetic field 18.

Two options X, Y are particularly suited for calculating the shim settings on the basis of the ascertained local homogeneity of the primary magnetic field 18. Further approaches that appear meaningful to those skilled in the art for calculating the shim settings are naturally also conceivable. A first option X provides that basic shim settings 18 are calculated on the basis of the ascertained local homogeneity of the basic magnetic field, wherein the calculation of the shim settings involves a fine adjustment of the basic shim settings. A second option Y provides that the calculation of the shim settings is performed under at least one marginal condition, wherein the at least one marginal condition requires a local minimum homogeneity of the primary magnetic field 18 at the position of the at least one marker element 36. The shim control unit can then pass the shim settings to the shim unit which can then be set on the basis of the shim settings for the acquisition of the magnetic resonance image data in the further method step 43.

As illustrated in FIG. 3, the adjustment of the image data acquisition scanner 13 involves a frequency adjustment of the image data acquisition scanner 13 and a setting of the image data acquisition scanner 13 using shim settings for the acquisition of the magnetic resonance image data by operation of the image data acquisition scanner 13. It should be emphasized here that both methods can also be employed independently of one another. The adjustment of the image data acquisition scanner 13 can also involve further measures appearing meaningful to those skilled in the art. The acquisition of the magnetic resonance image data in the further method step 43 can take place from the breast region of the subject under examination 15. A breast coil illustrated in FIG. 4 can be used for this purpose.

The method steps illustrated in FIG. 2 and FIG. 3 of the method according to the invention are carried out by the magnetic resonance device 11. For this purpose the magnetic resonance device 11 includes requisite software and/or computer programs which are stored in a storage unit of the computer unit 24 and/or of the control unit of the magnetic resonance device 11. The software and/or computer programs comprise program resources which are designed in order to carry out the method according to the invention when the computer program and/or the software is executed in the computer unit 24 and/or the control unit by means of a processor unit of the computer unit 24 and/or of the control unit.

Figure 4:
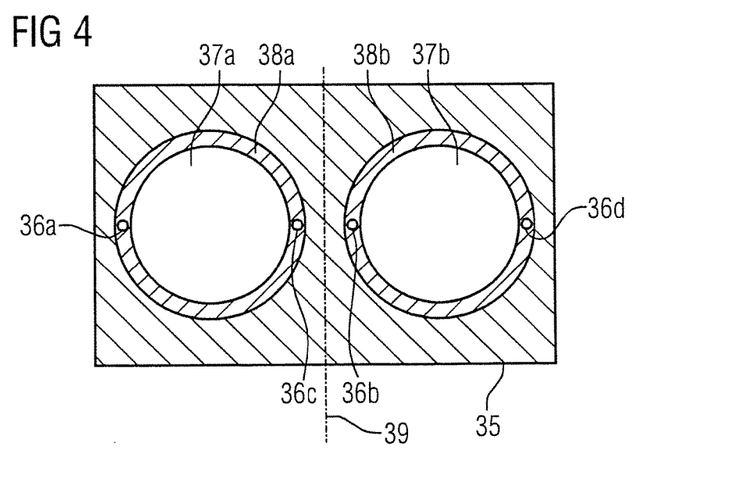
FIG. 4 shows an embodiment of a local coil according to the invention.

FIG. 4 shows an embodiment of a local coil 35 according to the invention. A coronal section through the local coil 35 is shown. The sectional plane in this case runs parallel to a support surface of a patient supporting device 16, on which the local coil 35 is positioned. It should be noted that the local coil 35 is illustrated only schematically.

In the case shown the local coil 35 is embodied as a breast coil. It thus has a first breast receiving area 37a for receiving a first breast of the subject under examination 15 and a second breast receiving area 37b for receiving a second breast of the subject under examination 15. Arranged around the first breast receiving area 37a is a first coil holder 38a which includes first coil elements (not illustrated) for receiving magnetic resonance signals emanating from the first breast. Arranged around the second breast receiving area 37b is a second coil holder 38b which includes second coil elements (not illustrated) for receiving magnetic resonance signals emanating from the second breast.

The breast coil illustrated includes four marker elements 36a, 36b, 36c, 36d. The four marker elements 36a, 36b, 36c, 36d exhibit a defined proportion of water and/or fat. By way of example the four marker elements 36a, 36b, 36c, 36d are embodied as reservoirs which are filled with 50 percent water and 50 percent fat. The breast coil can naturally include a different number of marker elements 36a, 36b, 36c, 36d.

A first marker element 36a and a third marker element 36c are secured to the first coil holder 38a in the immediate vicinity of the first breast receiving area 37a, in the present case in an edge region of the first breast receiving area 37a. A second marker element 36b and a fourth marker element 36d are secured to the second coil holder 38b in the immediate vicinity of the second breast receiving area 37b. At least one marker element 36a, 36b, 36c, 36d is thus arranged in each case on the first breast receiving area 37a and the second breast receiving area 37b.

The breast coil illustrated exhibits an axis of symmetry 39, wherein the first breast receiving area 37a on a first side of the axis of symmetry 39 and the second breast receiving area 37b on a second side of the axis of symmetry 39 are arranged symmetrically to each other with respect to the axis of symmetry 39. In this situation the axis of symmetry 39 likewise runs parallel to the support surface of the patient supporting device 16 on which the breast coil is positioned. The first marker element 36a is arranged symmetrically to the fourth marker element 36d with respect to the axis of symmetry 39. The third marker element 36c is arranged symmetrically to the second marker element 36b with respect to the axis of symmetry 39.

In the present exemplary embodiment the first and second breast receiving areas 37a, 37b each exhibit a first side which is facing towards the axis of symmetry 39, and a second side which is facing away from the axis of symmetry 39. In the case shown the four marker elements 36a, 36b, 36c, 36d are arranged in such a manner that the first marker element 36a is arranged at the first side of the first breast receiving area 37a, the second marker element 36b is arranged at the first side of the second breast receiving area 37b, the third marker element 36c is arranged at the second side of the first breast receiving area 37a and the fourth marker element 36d is arranged at the second side of the second breast receiving area 37b.

The breast coil shown is intended particularly for use in a method presented according to FIG. 2 or FIG. 3.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for obtaining magnetic resonance image data from a subject, comprising:

placing a subject, comprising tissue, at a tissue position in the subject, having a known tissue composition, in an imaging volume of a magnetic resonance scanner together with at least one marker element at a marker position on the subject that corresponds as closely as possible to said tissue position in the subject, said marker element having a marker composition corresponding to said tissue composition;

operating the magnetic resonance scanner to radiate a radio-frequency signal that excites nuclear spins in said marker element, thereby causing said marker element to emit magnetic resonance signals;

operating the magnetic resonance scanner to read out the magnetic resonance signals emitted by said marker element;

providing said magnetic resonance signals read out from said marker element to a control computer of said magnetic resonance scanner and, in said control computer, adjusting at least one operating parameter of said magnetic resonance scanner dependent on said magnetic resonance signals that have been read out from said marker element, thereby producing an adjusted magnetic resonance scanner; and with said control computer, operating said adjusted magnetic resonance scanner to acquire magnetic resonance image data from said tissue in the subject, and making the acquired magnetic resonance image data available in electronic form at an output of said control computer as a data file.

2. A method as claimed in claim 1 comprising operating said adjusted magnetic scanner to acquire said magnetic resonance image data from tissue in a breast region of the subject.

3. A method as claimed in claim 1 comprising using, as said marker element, a marker element comprising a defined proportion of at least one substance, storing a designation of said defined proportion in a database and, from said control computer, accessing said designation of said defined proportion from said database and adjusting said magnetic resonance scanner dependent on a relationship of said defined proportion to a proportion determined from the magnetic resonance signals that have been read out from said marker element.

4. A method as claimed in claim 3 comprising selecting said at least one substance from the group consisting of water and fat.

5. A method as claimed in claim 1 comprising adjusting said magnetic resonance scanner by adjusting a resonance frequency thereof.

6. A method as claimed in claim 5 comprising reading out said magnetic resonance signals from said marker element with a measuring frequency and with said marker element situated at a position in said magnetic resonance scanner, in said control computer, comparing said measuring frequency with a known marker element frequency of said marker element, and adjusting said resonant frequency of said magnetic resonance scanner dependent on a result of the comparison.

7. A method as claimed in claim 1 comprising adjusting said magnetic resonance scanner by adjusting shim settings thereof.

8. A method as claimed in claim 7 comprising generating said shim settings for said adjusted magnetic resonance scanner by determining, in said control computer, a local homogeneity of a basic magnetic field of said magnetic resonance scanner at a position of said marker element in said magnetic resonance scanner, from said magnetic resonance signals read out from said marker element, and calculating said shim settings dependent on said local homogeneity of said basic magnetic field.

9. A method as claimed in claim 8 comprising calculating said shim settings by making a fine adjustment of basic shim settings.

10. A method as claimed in claim 8 comprising calculating said shim settings dependent on at least one boundary condition that requires a local minimum homogeneity of said basic magnetic field at said position of said marker element.

11. A magnetic resonance apparatus comprising:
a magnetic resonance scanner comprising an imaging volume configured to receive a subject therein, said subject comprising tissue, at a tissue position in the subject, having a known tissue composition;
a marker element situated in said imaging volume together with said examination subject at a marker position on the subject that corresponds as closely as possible to said tissue position in the subject, said marker element having a marker composition corresponding to said tissue composition;
a control computer configured to operate the magnetic resonance scanner to radiate a radio-frequency signal that excites nuclear spins in said marker element, thereby causing said marker element to emit magnetic resonance signals;
said control computer configured to operate the magnetic resonance scanner to read out the magnetic resonance signals emitted by said marker element;
said control computer being configured to adjust at least one operating parameter of said magnetic resonance scanner dependent on said magnetic resonance signals that have been read out from said marker element, thereby producing an adjusted magnetic resonance scanner; and
said control computer being configured to operate said adjusted magnetic resonance scanner to acquire magnetic resonance image data from said tissue in the subject, and to make the acquired magnetic resonance image data available in electronic form at an output of said control computer as a data file.

* * * * *